US008859585B2

(12) United States Patent
Furey et al.

(10) Patent No.: US 8,859,585 B2
(45) Date of Patent: Oct. 14, 2014

(54) SCOPOLAMINE FOR THE TREATMENT OF DEPRESSION AND ANXIETY

(75) Inventors: Maura L. Furey, Silver Spring, MD (US); Wayne C. Drevets, Gaithersburg, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 2211 days.

(21) Appl. No.: 11/137,114

(22) Filed: May 25, 2005

(65) Prior Publication Data

US 2006/0270698 A1 Nov. 30, 2006

(51) Int. Cl.
*A01N 43/42* (2006.01)
*A61K 31/44* (2006.01)
*A61K 31/46* (2006.01)
*A61K 9/00* (2006.01)

(52) U.S. Cl.
CPC ................................ *A61K 31/46* (2013.01); *A61K 9/0073* (2013.01)
USPC ........................................ 514/304; 514/291

(58) Field of Classification Search
USPC ................................................ 514/291, 304
See application file for complete search history.

(56) References Cited

U.S. PATENT DOCUMENTS

2004/0087576 A1* 5/2004 Haracz ........................... 514/221
2006/0040900 A1* 2/2006 Neumeyer et al. ............... 514/80

FOREIGN PATENT DOCUMENTS

| CA | 1022930 | 12/1977 |
|----|---------|---------|
| DE | 3926751 | 2/1991 |
| WO | WO 98/31346 | 7/1998 |

OTHER PUBLICATIONS

Riedel et al. Psychopharmacologia, 1995, vol. 122, No. 2, pp. 1-2.*
Chau, D.T., et al., Nucleus Accumbens Muscarinic Receptors in the Control of Behavioral Depression: Antidepressant-Like Effects of Local $M_1$ Antagonist in the Porsolt Swim Test, *Neuroscience* 2001; 104(3):791-798.
Catholic Healthcare West, My Health Drug Reference, About Scopolamine, *Clinical Pharmacology Editorial Team*, 2002; 1-5.
Davis, K.L., et al., Physostigmine in Mania. *Archives of General Psychiatry*, 1978; 35: 119-122.
Delgado, P.L., How Antidepressants Help Depression: Mechanisms of Action and Clinical Response, *J Clin Psychiatry*, 2004; 65(4): 25-30.
Dilsaver, S.C., Pathophysiology of "Cholinoceptor Supersensitivity" in Affective Disorders. *Soc Biological Psychiatry*, 1986; 21: 813-829.

Ebert, U., et al., Scopolamine model of dementia: electroencephalogram findings and cognitive performance, *Eur J Clin Invest*, 1998; 28(11): 944-949.
Ebert, U., et al., Pharmacokinetics and Pharmacodynamics of Scopolamine after Subcutaneous Administration, *J Clin Pharmacology*, 1998; 38: 720-726.
Ebert, U., et al., Pharmacokinetic-Pharmacodynamic Modeling of the Electroencephalogram Effects of Scopolamine in Health Volunteers, *J Clin Pharmacol* 2001; 41:51-60.
Gillin, J.C., et al., The Effects of Scopolamine on Sleep and Mood in Depressed Patients with a History of Alcoholism and a Normal Comparison Group, *Biol Psychiatry* 1991; 30:157-169.
Janowsky, D.S. and D.H. Overstreet, The Role of Acetylcholine Mechanisms in Mood Disorders, *Psychopharmacology: The Fourth Generation of Progress*, Raven Press, 1995; 945-956.
Janowsky, D.S., et al., Cholinergic Reversal of Manic Symptoms, *The Lancet*, 1972; 1(7762):1236-1237.
Janowsky, D.S., et al., Effects of Physostigmine on Pulse, Blood Pressure, and Serum Epinephrine Levels, *American Journal of Psychiatry*, 1985; 142(6): 738-740.
Janowsky, D.S., et al., Acetylcholine and Depression, *Psychosomatic Medicine*, 1974; 36(3):248-257.
Janowsky, E.C., et al., Effects of Anesthesia on Patients Taking Psychotropic Drugs, *J. Clinical Psychopharmacology*, 1981; 1(1): 14-20.
Janowsky, D.S., et al., The Role of Acetylcholine Mechanisms in Affective Disorders, *Amer Coll Neuropsychopharmacology Journal: The Fourth Generation of Progress*, 2000; 1-15.
Newhouse, P.A., The Effects of Acute Scopolamine in Geriatric Depression, *Arch Gen Psychiatry*, 1988; 45(10):906-912.
Nurnberger, J.I., Jr., et al., Behavioral, Physiological, and Neuroendocrine Responses to Arecoline in Normal Twins and "Well State" Bipolar Patients, *Psychiatry Research*, 1983; 9(3):191-200.
Owens, M.J., Selectivity of Antidepressants: From the Monoamine Hypothesis of Depression to the SSRI Revolution and Beyond, *J Clin Psychiatry*, 2004; 65(4): 5-10.
Pacher, P. and Kecskemeti, V., Trends in the Development of New Antidepressants. Is there a Light at the End of the Tunnel? *Current Medicinal Chemistry*, 2004; 11: 925-943.
Payk, T.R., Treatment of Depression, *J Geriatr Psychiatry Neurol*, 1994; 7(1) S3-S5.
Poland, R.E., et al., Differential Response of Rapid Eye Movement Sleep to Cholinergic Blockade by Scopolamine in Currently Depressed, Remitted, and Normal Control Subjects, *Biol Psychiatry*, 1997; 41(9): 929-938.
Preskorn, S. H., Rational Drug Discovery of SSRI's. Clinical Pharmacology of SSRI's, *Ed: S. H. Preskorn, Professional Communications, Inc.*, 1996; 15-32.

(Continued)

*Primary Examiner* — Samira Jean-Louis
(74) *Attorney, Agent, or Firm* — Klarquist Sparkman, LLP

(57) ABSTRACT

Provided are methods and compositions for the treatment of depression and anxiety. The compositions contain scopolamine, or an analog thereof, and can optionally include one or more psychoactive agents. Further provided is an inhaler containing scopolamine, or an analog thereof, in a pharmaceutically acceptable carrier.

18 Claims, 3 Drawing Sheets

(56) References Cited

OTHER PUBLICATIONS

Raisman, R., et al., Specific tricyclic antidepressant binding sites in rat brain, *Nature*, 1979; 281: 48-150.

Richelson, E., Antimuscarinic and Other Receptor-Blocking Properties of Antidepressants, *Mayo Clinic Proc*, 1983; 58: 40-46.

Risch, S.C., et al., Cholinergic Challenges in Affective Illness: Behavioral and Neuroendocrine Correlates, *J Clinical Psychopharmacology*, 1981; 1(4): 186-192.

Rubin, R.T., et al., Hypothalamo-pituitary-adrenal cortical responses to low-dose physostigmine and arginine vasopressin administration: sex differences between major depressives and matched control subjects, *Psychiatry Research*, 1999; 89(1): 1-20.

Schatzberg, A.F., Pharmacologic Treatments of Major Depression: Are Two Mechanisms Really Better Than One? *J Clin Psychiatry*, 2004; 65:(4) 3-4.

Stanton, T., et al., Antagonism of the five cloned human muscarinic cholinergic receptors expressed in CHO-K1 cells by antidepressants and antihistaminics, *Biochemical Pharmacology*, 1993; 45(11): 2352-2354.

Zajecka, J.M., et al., SNRIs in the Management of Acute Major Depressive Disorder, *J Clin Psychiatry*, 2004; 65(17): 11-18.

PCT/US06/19335, May 18, 2006, National Institutes of Health, Written Opinion of the International Searching Authority, Oct. 13, 2006.

PCT/US06/19335, May 18, 2006, National Institutes of Health, International Search Report, Oct. 13, 2006.

Rush, Douglas K., "Scopolamine Amnesia of Passive Avoidance: A Deficit of Information Acquisition," *Behavioral and Neural Biology*, vol. 50, pp. 255-274 (1988).

Safer et al., "The Central Effects of Scopolamine in Man," *Biological Psychiatry*, vol. 3, pp. 347-355 (1971).

Drevets and Furey, "Replication of Scopolamine's Antidepressant Efficacy in Major Depressive Disorder: A Randomized Placebo-Controlled Clinical Trial," *Biol. Psychiatry*, vol. 67, pp. 432-438, 2010.

Furey and Drevets, "Antidepressant Efficacy of the Antimuscarinic Drug Scopolamine: A Randomized Placebo-Controlled Clinical Trial," *Arch. Gen. Psychiatry*, vol. 63, pp. 1121-1129, 2006.

\* cited by examiner

SCOPOLAMINE FOR THE TREATMENT OF DEPRESSION AND ANXIETY

ACKNOWLEDGEMENTS

This invention was made with government support under Grant 03-M-0108 awarded by National Institutes of Health. The government has certain rights in the invention.

BACKGROUND OF THE INVENTION

1. Field of the Invention

This invention relates generally to the field of treatment of depression and anxiety in subjects diagnosed with depression and anxiety. Specifically, the invention relates to the treatment of depression and anxiety with scopolamine, or analogs thereof.

2. Background Art

Despite the availability of a wide range of antidepressant drugs, clinical trials indicate that 30% to 46% of patients with major depression fail to respond to first-line antidepressant treatment, despite adequate dosage, duration, and compliance. Moreover, in those patients who do experience symptomatic relief following conventional anti-depressant treatment, clinical improvement is not evident for 3-4 weeks.

Some effective antidepressant medications such as tricylic antidepressant drugs have potent antimuscarinic effects [7-9]; however, there has been no study to evaluate systematically the efficacy of an anticholinergic as an antidepressant agent. Successful clinical treatment of depression has depended on the use of tricyclic agents, monoamine oxidase inhibitors and selective serotonin reuptake inhibitors (SSRI). Moreover, over the past two decades of antidepressant drug development, the muscarinic antagonist effects of early antidepressant drugs (i.e., the tricyclic antidepressant agents) were viewed almost exclusively as producing unwanted side effects without contributing at all to therapeutic effects [14-16]. As a result, efforts to develop new antidepressant treatments included an emphasis on developing compounds that specifically did not have antagonist effects at muscarinic cholinergic receptors [17].

SUMMARY OF THE INVENTION

In accordance with the purposes of this invention, as embodied and broadly described herein, this invention, in one aspect, relates to a method of treating major depressive disorder in a subject diagnosed with major depressive disorder, comprising administering to the subject a composition comprising a therapeutically effective amount of scopolamine, or an analog thereof, in a pharmaceutically acceptable carrier, whereby the administration of the composition treats major depressive disorder in the subject.

In another aspect, the invention relates to a method of treating treatment-resistant major depressive disorder in a subject diagnosed with treatment-resistant major depressive disorder, comprising administering to the subject a composition comprising a therapeutically effective amount of scopolamine, or an analog thereof, in a pharmaceutically acceptable carrier, whereby the administration of the composition treats treatment-resistant major depressive disorder in the subject.

In yet another aspect, the invention relates to a method of treating depressed phase of bipolar disorder in a subject diagnosed with depressed phase of bipolar disorder, comprising administering to the subject a composition comprising a therapeutically effective amount of scopolamine, or an analog thereof, in a pharmaceutically acceptable carrier, whereby the administration of the composition treats depressed phase of bipolar disorder in the subject.

In another aspect, the invention relates to a method of treating panic disorder in a subject diagnosed with panic disorder, comprising administering to the subject a composition comprising a therapeutically effective amount of scopolamine, or an analog thereof, in a pharmaceutically acceptable carrier, whereby the administration of the composition treats panic disorder in the subject.

In another aspect, the invention relates to a method of treating social phobia (social anxiety disorder) in a subject diagnosed with social phobia (social anxiety disorder), comprising administering to the subject a composition comprising a therapeutically effective amount of scopolamine, or an analog thereof, in a pharmaceutically acceptable carrier, whereby the administration of the composition treats social phobia (social anxiety disorder) in the subject.

In another aspect, the invention relates to a method of treating post-traumatic stress disorder in a subject diagnosed with post-traumatic stress disorder, comprising administering to the subject a composition comprising a therapeutically effective amount of scopolamine, or an analog thereof, in a pharmaceutically acceptable carrier, whereby the administration of the composition treats post-traumatic stress disorder in the subject.

In yet another aspect, the invention relates to a method of treating generalized anxiety disorder in a subject diagnosed with generalized anxiety disorder, comprising administering to the subject a composition comprising a therapeutically effective amount of scopolamine, or an analog thereof, in a pharmaceutically acceptable carrier, whereby the administration of the composition treats generalized anxiety disorder in the subject.

In another aspect, provided is an inhaler comprising a composition comprising scopolamine, or an analog thereof, in a pharmaceutically acceptable carrier.

In yet another aspect, provided is a kit comprising an inhaler comprising a composition comprising scopolamine, or an analog thereof, in a pharmaceutically acceptable carrier, and instructions regarding using the inhaler.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Thus, provided herein are compositions and improved methods for quickly and efficiently treating unipolar and bipolar depression with scopolamine, or an analog thereof, an anticholinergic agent that relieves depression without producing unwanted side effects usually associated with such agents.

BRIEF DESCRIPTION OF THE DRAWINGS

The accompanying drawings, which are incorporated in and constitute a part of this specification, illustrate several embodiments of the invention and together with the description, serve to explain the principles of the invention.

Figure 1:
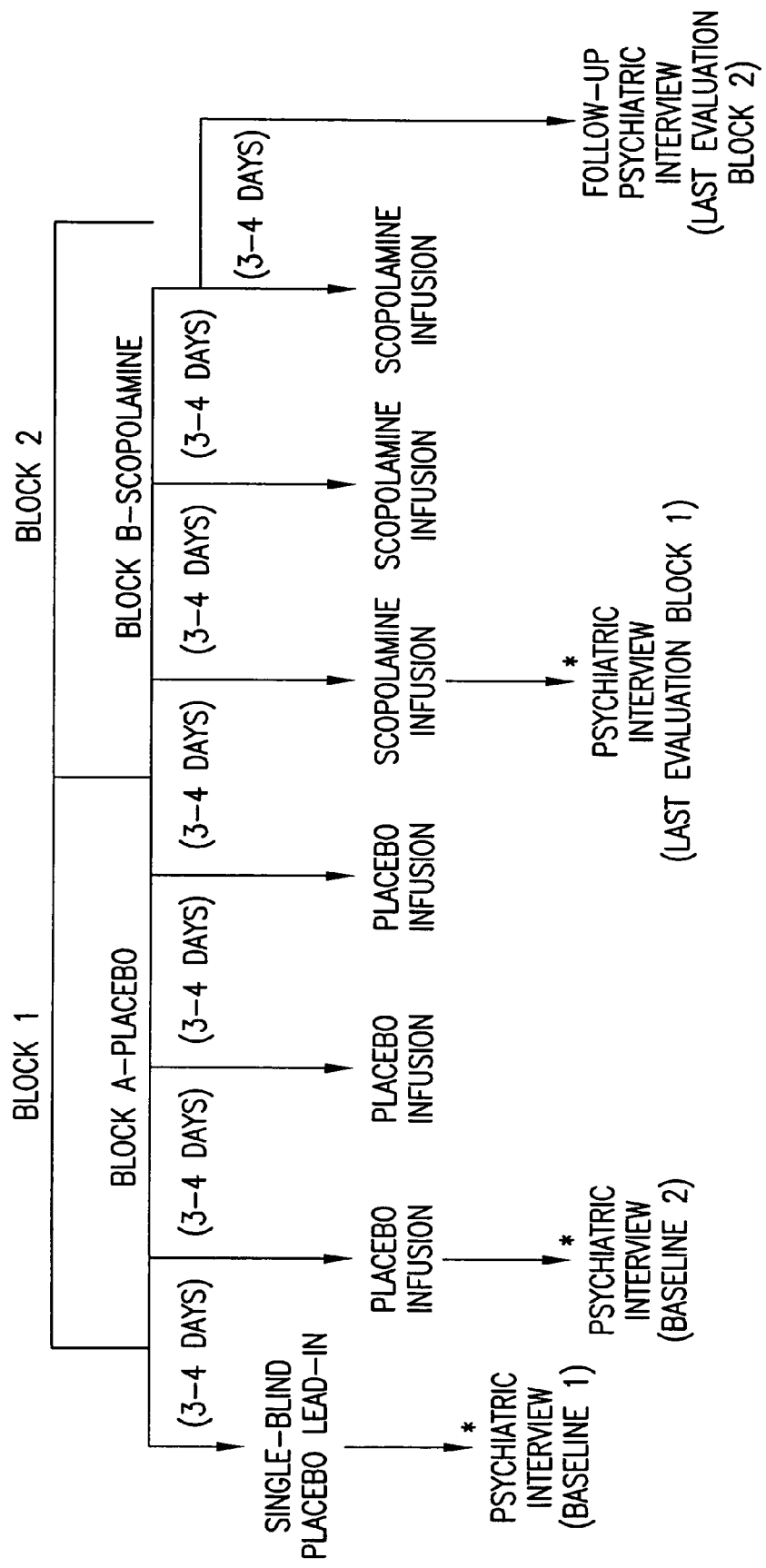
FIG. 1 shows a study that included a series of seven sessions, each involving a 15-minute intravenous infusion of either a placebo saline solution, or 4 µg/kg of scopolamine.

Session one was designed to single-blind during which all subjects received a placebo infusion to allow for a baseline evaluation. The next six sessions were separated into two blocks of three sessions each; one block included a series of three placebo infusions (P Block) and the other a series of three scopolamine infusions (S Block). Individuals were randomized into either the P/S (placebo/scopolamine) series or the S/P (scopolamine/placebo) series, using a double-blind design. In total, all subjects received four placebo infusions and three scopolamine infusions. Prior to infusion, unstructured psychiatric interviews were completed using the Montgomery & Asberg Depression Rating Scale (MADRS) and the Hamilton Anxiety Scale to provide evaluations of depression and anxiety severity upon entering the study (i.e., baseline 1); following the first infusion as an assessment of placebo effects (i.e., baseline 2); after all infusions associated with block 1 (i.e., last evaluation block 1); and after all infusions associated with block 2 (i.e., last evaluation block 2) obtained during a follow-up psychiatric interview. Sessions were scheduled a minimum of 3 days apart and a maximum of 5 days apart when possible.

Figure 2:
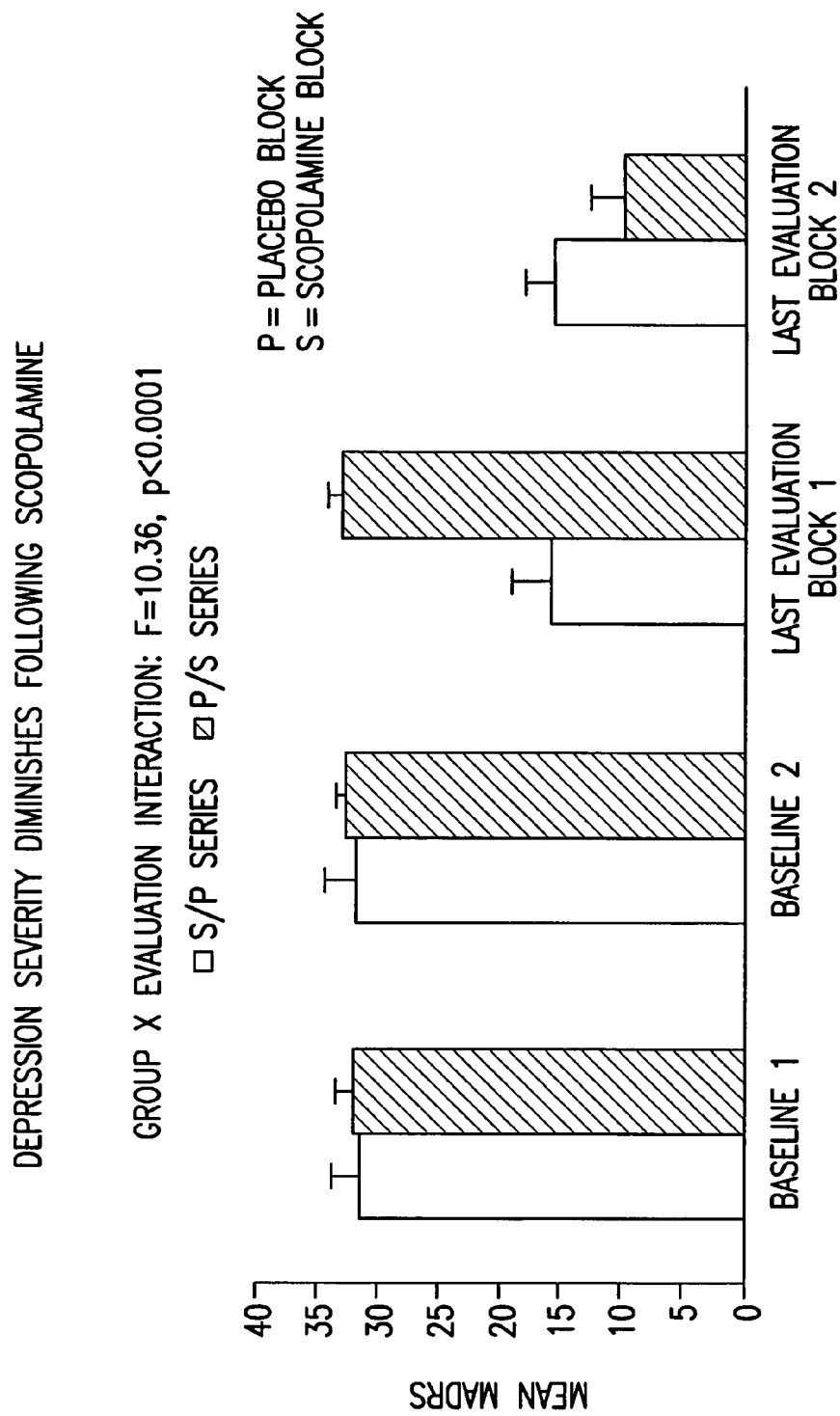

FIG. 2 shows Mean MADRS scores (±standard error) in association with each of the four psychiatric evaluations. Patients in both treatment groups showed significant improvement in depressive symptoms following treatment with scopolamine, but no change in symptoms following placebo.

Figure 3:
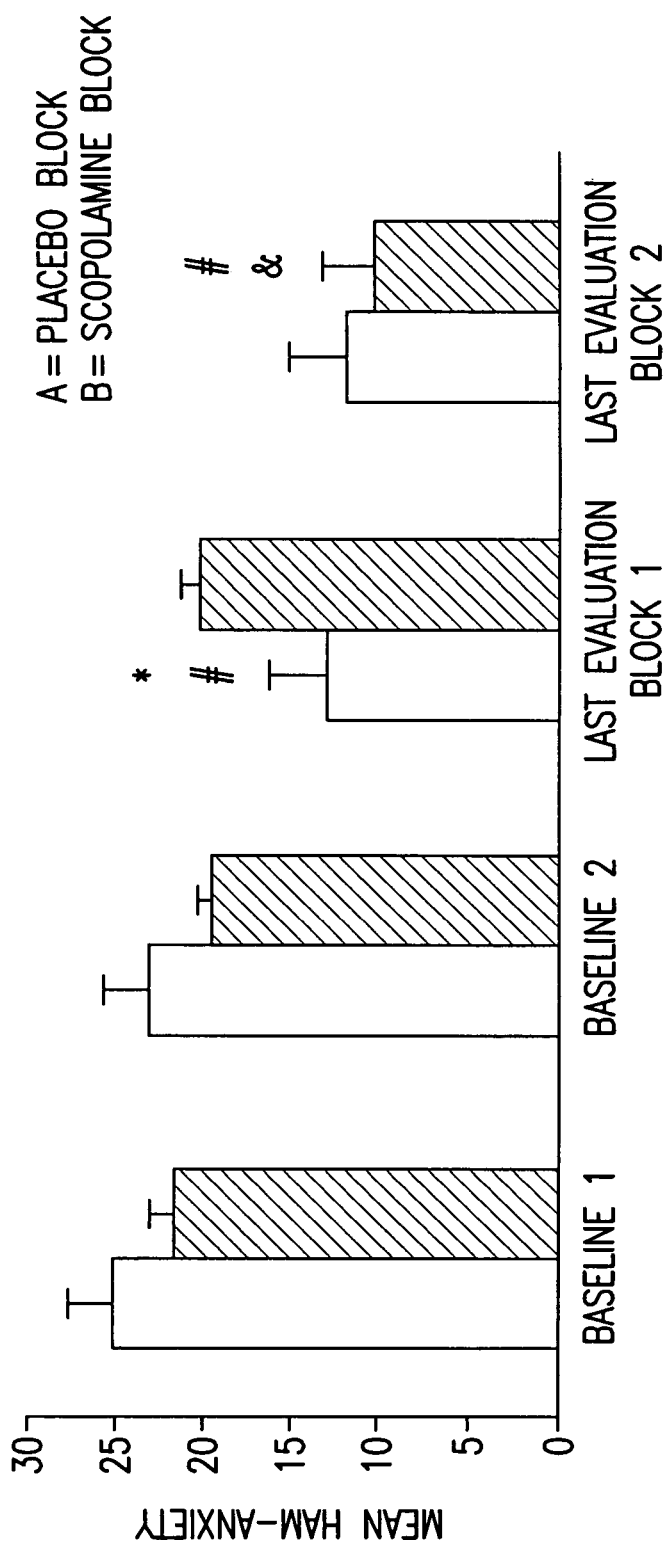

FIG. 3 shows Mean Hamilton Anxiety scores (±standard error) in association with each of the four psychiatric evaluations. Patients in both treatment groups showed significant improvement in anxiety symptoms following treatment with scopolamine, but no change in symptoms following placebo.

DESCRIPTION OF THE PREFERRED EMBODIMENTS

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

Disclosed are the various compounds, solvents, solutions, carriers, and/or components to be used to prepare the disclosed compositions as well as the compositions themselves to be used within the methods disclosed herein. Also diclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, that while specific reference of each various individual and collective combination and permutation of these compounds may not be explicitly disclosed, each is specifically contemplated and described herein.

Likewise, it is further understood that any of the various compounds, solvents, solutions, carriers, components, steps, elements, amounts, routes of administration, symptoms, treatments, or combinations or permutations thereof—whether explicitly or implicitly disclosed—are specifically contemplated and described herein and, further, can be specifically excluded from the disclosed compositions or methods.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

As used in the specification and the appended claims, the singular forms "a," "an" and "the" include plural referents unless the context clearly dictates otherwise. Thus, for example, reference to "an analog of scopolamine" includes mixtures of analogs of scopolamine, and reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 1" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined herein as follows:

"Optional" or "optionally" means that the subsequently described event or circumstance may or may not occur, and that the description includes instances where said event or circumstance occurs and instances where it does not. For example, the statement "optionally the composition further comprises a therapeutically effective amount of one or more psychoactive agents" means that the composition may or may not comprise one or more psychoactive agents and that the description includes both a composition comprising one or more psychoactive agents and a composition not comprising one or more psychoactive agents.

Major depressive disorder (MDD) is a common disorder of mood and affect characterized by one or more major depressive episodes. These episodes are defined diagnostically using a criteria-based syndrome listed and described in the Diagnostic and Statistical Manual Series, Fourth Edition (DSM-IV) (American Psychiatric Association Press, Washington, D.C., 1994). These episodes are diagnosed in a human patient if the patient has experienced 5 symptoms from a list of 9 symptom categories every day, or nearly every day, for a period lasting at least 2 weeks. At least one symptom must be present from either category 1 (having a sad, depressed, empty, or irritable mood, or appearing sad to others), or category 2 (experiencing loss of interest in or pleasure from activities). The other symptom categories include: 3) change in weight and/or appetite, 4) insomnia or hypersomnia, 5) psychomotor agitation or retardation, 6) fatigue and/or loss of energy, 7) feelings of worthlessness and/or excessive or inappropriate guilt, 8) diminished ability to think or of concentrate and/or indecisiveness, and 9) recurrent thoughts of death or suicide.

The diagnostic terms and codes from DSM-IV are Major depressive disorder, single episode: DSM IV-296.2; and Major depressive disorder, recurrent: DSM IV-296.3. These diagnostic categories also are codified in the International Classification of Diseases, Version 10 (World Health Organization; http://www3.who.int/icd/vollhtm2003/fr-icd.htm), where they encompass the F32 and F33 conditions.

Bipolar Disorder (also known as "manic-depressive illness") is a mood disorder arising in a human patient who experiences major depressive episodes which alternate with episodes of mania (in the case of type I) or hypomania (in the case of type II). These episodes are defined diagnostically using a criteria-based syndrome listed and described in the DSM-IV. Mania is a syndrome characterized by a euphoric, expansive, or irritable mood lasting at least one week. In addition, at least three of the following symptoms persisted during the same time period: inflated self esteem and/or grandiosity, decreased need for sleep, increased volume or rate of speech, flight of ideas and/or racing thoughts, distractibility, increased goal-directed activity and/or psychomotor agitation, excessive involvement in pleasurable activities that have a high potential for painful consequences. Mania and hypomania have similar signs and symptoms but are distinguished by the degree to which they result in impaired social and occupational functioning.

The conventional diagnostic terms and criteria for the depressed phase of bipolar disorder are listed in the DSM-IV; Bipolar I Disorder, Most Recent Episode Depressed: DSM IV-296.5; and Bipolar II Disorder, (Recurrent Major Depressive Episodes With Hypomanic Episodes): DSM IV-296.89. They also are codified in the International Classification of Diseases, Version 10 (World Health Organization; http://www3.who.int/icd/vollhtm2003/fr-icd.htm), where they encompass the F31.3 and F31.4 conditions.

Bipolar affective disorder is characterized by two or more episodes in which the patient's mood and activity levels are significantly disturbed, this disturbance consisting on some occasions of an elevation of mood and increased energy and activity (hypomania or mania) and on others of a lowering of mood and decreased energy and activity (depression). Repeated episodes of hypomania or mania only are classified as bipolar. This includes manic depressive illness, psychosis, and reaction. This excludes bipolar disorder, single manic episode (F30.-) and cyclothymia (F34.0).

In Bipolar affective disorder (F31.3), current episode mild or moderate depression, the patient is currently depressed, as in a depressive episode of either mild or moderate severity (F32.0 or F32.1), and has had at least one authenticated hypomanic, manic, or mixed affective episode in the past.

In Bipolar affective disorder (F31.4), current episode severe depression without psychotic symptoms, the patient is currently depressed, as in severe depressive episode without psychotic symptoms (F32.2), and has had at least one authenticated hypomanic, manic, or mixed affective episode in the past.

Treatment-resistant depression is exemplified by a case in which a human patient with either major depressive disorder or bipolar disorder continues to meet criteria for a major depressive episode in spite of treatment with conventional antidepressant drugs at adequate doses and treatment durations (at least 4 to 8 weeks).

Panic Disorder is an episodic paroxysmal anxiety syndrome characterized by recurrent attacks of severe anxiety (panic) which are not restricted to any particular situation or set of circumstances and are therefore unpredictable. The symptoms include sudden onset of palpitations, chest pain, dyspnea, dizziness, and feelings of unreality (depersonalization or derealization). There is often also a secondary fear of dying, losing control, or going insane. Panic disorder may be seen with or without agoraphobia, which is characterized by a cluster of phobias embracing fears of leaving home, entering shops, crowds and public places, or traveling alone in trains, buses or planes. Avoidance of the phobic situation is prominent, to an extent that agoraphobics alter their lifestyles to avoid their relevant phobic situations.

The conventional diagnostic criteria for panic disorder are listed in the DSM-IV as Panic Disorder Without Agoraphobia: DSM IV-300.01; and Panic Disorder With Agoraphobia: DSM IV-300.21. Panic disorders also are codified in the International Classification of Diseases, Version 10 (World Health Organization; http://www3.who.int/icd/vollhtm2003/fr-icd.htm), where they encompass F40.0 (Panic Disorder With Agoraphobia) and F41.0 (Panic Disorder) conditions.

Social phobia (also called Social Anxiety Disorder) is characterized by a marked and persistent fear of one or more social or performance settings in which the patient is exposed to unfamiliar people or to possible scrutiny by other people. The patient fears that in such situation they will act in a way (or show anxiety symptoms) that will be humiliating or embarrassing. Exposure to the feared social situation almost invariably provokes anxiety, and this response may progress to panic attacks. The feared social or performance situations are avoided, or else are endured with intense anxiety and distress.

The conventional diagnostic criteria for social phobia are listed in the DSM-IV as Social Phobia (Social Anxiety Disorder): DSM IV-300.23. Social phobia also is codified in the International Classification of Diseases, Version 10 (World Health Organization; http://www3.who.int/icd/vollhtm2003/fr-icd.htm), as condition F40.1.

Post-traumatic stress disorder arises as a delayed or protracted response to a stressful event or situation (of either brief or long duration) of an exceptionally threatening or catastrophic nature which is likely to cause pervasive distress in almost anyone. Predisposing factors, such as personality traits or previous history of mood or anxiety disorders, may lower the threshold for the development of the syndrome or aggravate its course, but they are neither necessary nor sufficient to explain its occurrence. Typical features include episodes of repeated reliving of the trauma in intrusive memories ("flashbacks"), dreams or nightmares occurring against the persisting background of a sense of "numbness" and emotional blunting, detachment from other people, unresponsiveness to surroundings, anhedonia, and avoidance of activities and situations reminiscent of the trauma. There often is a state of autonomic hyperarousal with hypervigilance, an enhanced startle reaction, and insomnia. Anxiety and depression commonly are associated with these symptoms and signs. The onset follows the trauma with a latency period that may range from a few weeks to months.

The conventional diagnostic criteria for social phobia are listed in the DSM-IV as Post-Traumatic Stress Disorder: DSM IV-309.81. Post-traumatic stress disorder also is codified in the International Classification of Diseases, Version 10

(World Health Organization; http://www3.who.int/icd/vollhtm2003/fr-icd.htm), as condition F43.1.

Generalized Anxiety Disorder is a chronic anxiety syndrome characterized by excessive worry or anxiety over a period lasting at least 6 months. These symptoms are associated with at least 3 of the following 6 symptoms: 1) restlessness or feeling on edge, 2) feeling easily fatigued, 3) impaired concentration, 4) irritability, 5) muscle tension, and 6) sleep disturbance. These anxiety symptoms are generalized and persistent but not restricted to, or even strongly predominating in, any particular environmental circumstances. The anxiety syndrome is sufficiently severe to cause clinically significant distress or to impair social or occupational functioning. The conventional diagnostic criteria for generalized anxiety disorder are listed in the DSM-IV as Generalized Anxiety Disorder: DSM IV-300.02. Generalized Anxiety Disorder also is codified in the International Classification of Diseases, Version 10 (World Health Organization; http://www3.who.int/icd/vollhtm2003/fr-icd.htm), as condition F41.1.

Compositions

Disclosed herein, in one aspect, are compositions and methods that utilize scopolamine, or analogs thereof. By "scopolamine analogs" is meant a class of muscarinic receptor antagonist that includes the belladonna alkaloids or semisynthetic or synthetic analogs thereof. Scopolamine, one member of this class, is represented by Formula I.

I (scopolamine)

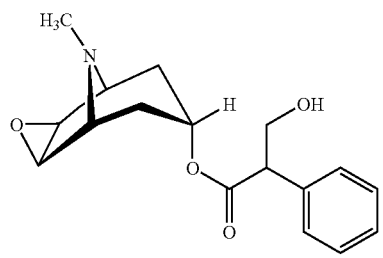

It is understood, that the phrase "scopolamine analogs," includes compounds that generally have the same backbone as scopolamine, as shown in Formula I, but where various moieties have been substituted or replaced by other substituents or moieties. As used herein, the terms "substituted" and "replaced" are contemplated to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valencies of the heteroatoms. This disclosure is not intended to be limited in any manner by the permissible substituents of organic compounds. Also, the terms "substituted" or "replaced" include the implicit proviso that such substitution or replacement is in accordance with permitted valence of the substituted atom and the substituent, and that the substitution or replacement results in a stable compound, e.g., a compound that does not spontaneously undergo transformation such as by rearrangement, cyclization, elimination, etc.

Some examples of scopolamine analogs that can be used in the compositions and methods disclosed herein include, but are not limited to, salts of scopolamine with various acids, such as hydrochloric acid, hydrobromic acid, hydroiodic acid, nitric acid, phosphoric acid, sulfuric acid, and the like. In one aspect, a suitable scopolamine analog can be scopolamine hydrobromide.

Additional examples of scopolamine analogs include, but are not limited to, N-alkylated analogs of scopolamine, that is, analogs containing an alkyl substituent attached to the nitrogen atom, forming a quaternary ammonium species. By "alkyl" is meant a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl, and the like. The alkyl group can also be substituted or unsubstituted. Some specific examples of N-alkylated analogs of scopolamine include, but are not limited to, those represented by Formulae II, III, and IV.

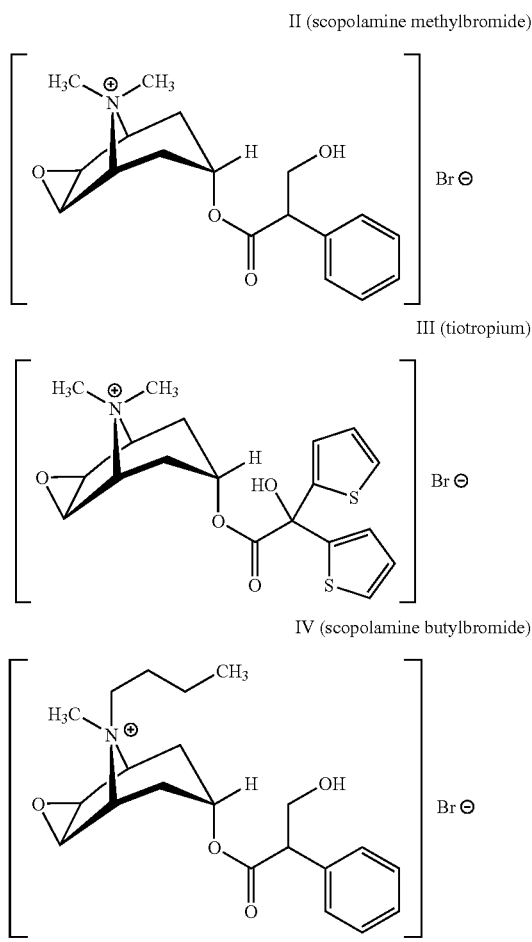

Also included are other salts (e.g., pharmaceutically acceptable salts) of such N-alkylated scopolamine analogs.

Still further examples of scopolamine analogs include, but are not limited to, un-epoxylated analogs of scopolamine, that is, analogs where the epoxy group in Formula I is removed. One example of such an analog is atropine, which is represented by Formula IV.

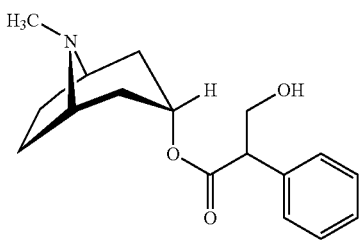

IV (atropine)

Like scopolamine, atropine has various salt and N-alkylated analogs. These atropine analogs are described herein and are intended to be included by the phrase "scopolamine, or analogs thereof." As such, further examples of scopolamine analogs include, but are not limited to, analogs of atropine with various salts (e.g., atropine hydrobromide, atropine hydrochloride, and the like) and N-alkylated analogs of atropine (e.g., atropine methyl bromide). Also included are homatropine and its salts and N-alkylated analogs. Some specific examples of scopolamine analogs are the atropine analogs represented by Formulae V and VI.

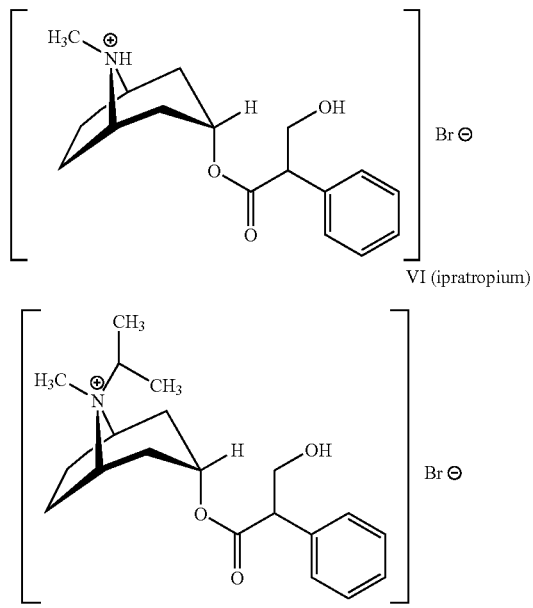

V (atropine hydrobromide)

VI (ipratropium)

A list of suitable scopolamine analogs that can be used in the disclosed compositions and methods, including their commercial brand names, includes, but is not limited to, atropine, atropine hydrobromide, atropine oxide hydrochloride, atropine sulfate, belladonna, scopolamine, scopolamine hydrobromide, scopolamine methylbromide, scopolamine butylbromide, homatropine, ipratropium, tiotropium, hyoscyamine sulfate, methscopolamine, methscopolamine bromide, homatropine hydrobromide, homatropine methylbromide, hyoscyamine, hyoscyamine hydrobromide, hyoscyamine sulfate, propantheline bromide, anisotropine, anisotropine methylbromide, methantheline bromide, emepronium bromide, clindinium, clidinium bromide, hyoscine, hyoscine butylbromide, hyoscine hydrobromide, hyoscine methobromide, hyoscine methonitrite, hyoscyamine, hyoscyamine sulfate, buscapine, buscolysin, buscopan, butyiscopolamine, hyoscine N-butylbromide, N-butylscopammonium bromide, scopolan bromide, butylscopolammonium bromide, N-butylscopolammonium chloride, hyoscine N-butylbromide, DD-234, hyoscine methiodide, hyoscine methobromide, methyiscopolamine nitrate, methylscopolammoium methylsulfate, N-methylscine methylsulfate, N-methylscopolamine bromide, N-methylscopolamine iodide, N-methylscopolamine methylchloride, N-methylscopolamine methylsulfate, N-methylscopolamine nitrate, skopyl, ulix bromide, N-methylscopolamine, N-methylscopolamine methobromide, scopolamine methylchloride, N-methylscine methylsulfate, tematropium methylsulfate, and N-isopropylatropine, including salts and derivatives thereof.

Other compounds, which are cholinergic receptor antagonists, can also be used in the disclosed compositions and methods. A list of such suitable compounds includes, but is not limited to, pirenzepine, AF-DX 116, methoctramine, oxyphencyclimine, propantheline, tridihexethyl, dicyclomine, cylopentolate, tropicamide, trihexylphenidyl, benztropine, orphenadrine, ethopropazine, dipehnhydramine, cycrimine, biperiden, hexocyclim, isopropamide, mepenzolate, propantheline bromide, imipramine, mepenzolate bromide, isopropamide iodide, clidinium bromide, including salts and derivatives thereof. In one specific example, a suitable cholinergic receptor antagonist that can be used in the compositions and methods disclosed herein is pirenzepine, represented by Formula VII, and salts and derivatives thereof.

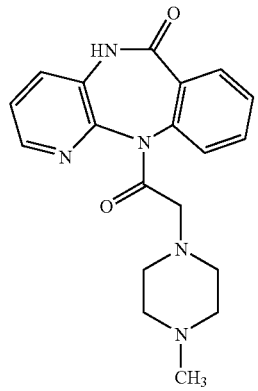

VII (pirenzepine)

Still further examples of other cholinergic receptor antagonists that can be used in the disclosed compositions and methods, including the commercial brand names, include, but are not limited to, alverinc citrate, benapryzine hydrochloride, benzetimide hydrochloride, benzilonium bromide, biperiden, biperiden hydrochloride, biperiden lactate, cyclopentolate hydrochloride, dexetimide, dicyclomine hydrochloride, dihexyverine hydrochloride, domazoline fumarate, elantrine, elucaine, ethybenztropine, eucatropine hydrochloride, glycopyrrolate, heteronium bromide, isopropamide iodide, mepenzolate bromide, methylatropine nitrate, metoquizine, oxybutynin chloride, parapenzolate bromide, pentapiperium methylsulfate, phencarbamide, poldine methylsulfate, proglumide, propantheline bromide, propenzolate hydrochloride, tiquinamide hydrochloride, tofenacin hydrochloride, toquizine, triampyzine sulfate, trihexyphenidyl hydrochloride, and tropicamide, including salts and derivatives thereof.

Still other examples of cholinergic receptor antagonists that can be used in the disclosed compositions and methods include, but are not limited to, quinuclidinone methyliodide, N-methyl-3-hydroxyl-quinnuclidinium iodide, 3-quinuclidinyl acetat hydrochloride, 3-quincuoliny benzoate hydrochloride, 3-quinuclidinyl benzilat, N-methyl-3-[(cyclohexylhydroxy-phenylacetyl)oxy]quinuclidinium bromide, N-methyl-3-quinuclidinyl benzilat bromide, alpha-methyl-alpha-phenylbenzene-acetic acid quinuclidin-3-yl ester hydro-chloride, [R—(R*,R*)]alpha-(Hydroxymethyl)-alpha-phenyl-1H-imidazole-1-acetic acid quinuclidine-3-yl ester, [R—(Z)]-(+)-a-(quinuclidin-3-yl)-a-(methoximino) acetonitril, 3-(3-Hexyloxy-pyrazin-2-ylsulfanyl) quinuclidine, 3(R)-[2-(6-trifluoromethylpyrazin)yl]quinuclidine, and (3R)-3-(6-chloropyrazin-2-yl) quinuclidine, including salts and derivatives thereof.

Also, pharmaceutically acceptable salts or esters of the above described compounds are disclosed herein and can be used in the compositions and methods disclosed herein. By "pharmaceutically acceptable salts or esters" is meant a material that is not biologically or otherwise undesirable, i.e., the material can be administered to an individual along with the selected compound without causing any undesirable biological effects or interacting in a deleterious manner with any of the other components of the pharmaceutical composition in which it is contained. Described herein are the pharmaceutically acceptable salts or esters of the above listed compounds, including those represented by Formulae I-VII.

Pharmaceutically acceptable salts are prepared by treating a compound with an appropriate amount of a pharmaceutically acceptable base. Representative pharmaceutically acceptable bases include ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C., such as at room temperature. The molar ratio of compounds to be used is chosen to provide the ratio desired for any particular salts. For preparing, for example, the bromide salts of the various compounds, the compounds can be treated with approximately one equivalent of pharmaceutically acceptable base to yield a neutral salt. Pharmaceutically acceptable esters include, but are not limited to, methyl, ethyl, propyl, butyl, pentyl, hexyl, cyclopropyl, cyclobutyl, cyclopentyl, cyclohexyl, cycloheptyl, cyclopentenyl, cyclopentadienyl, cyclohexenyl, cyclohexadienyl, phenyl, pyridinyl, benzyl, and the like. Pharmaceutically acceptable esters can be prepared by, for example, by treating the compound with an appropriate amount of carboxylic acid, ester, acid chloride, acid anhydride, or mixed anhydride agent that will provide the corresponding pharmaceutically acceptable ester. Typical agents that can be used to prepare pharmaceutically acceptable esters include, for example, acetic acid, acetic anhydride, acetyl chloride, benzylhalide, benzaldehyde, benzoylchloride, methyl ethylanhydride, methyl phenylanhydride, methyl iodide, and the like.

The compounds disclosed herein, including scopolamine and analogs thereof, can be obtained commercially or can be readily synthesized using techniques generally known to those of skill in the art. The starting materials and reagents used in preparing these compounds are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, $4^{th}$ Edition); and Larock's Comprehensive Organic Transformations (VCH Publishers Inc., 1989).

Methods

Provided herein is a method of treating major depressive disorder in a subject diagnosed with major depressive disorder, comprising administering to the subject a composition comprising a therapeutically effective amount of scopolamine, or an analog hereof, in a pharmaceutically acceptable carrier, whereby the administration of the composition treats major depressive disorder in the subject.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

The terms "administering" and "administration" refer to methods of providing a pharmaceutical preparation to a subject. Such methods are well known to those skilled in the art and include, but are not limited to, administering the compositions orally, parenterally (e.g., intravenously and subcutaneously), by intramuscular injection, by intraperitoneal injection, intrathecally, transdermally, extracorporeally, topically or the like.

A composition can also be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition comprising scopolamine, or an analog thereof, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, for uxample, U.S. Pat. No. 3,610,795, which is incorporated by reference herein.

A "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in Remington: The Science and Practice of Pharmacy (19th ed.) Gennaro, ed., Mack Publishing Company, Easton, Pa., 1995, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, antiinflammatory agents, anesthetics, and the like.

The pharmaceutical formulation can be administered in a number of ways depending on whether local or systemic treatment is desired, and on the area to be treated. Administration may be topically (including ophthahnically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids or binders may be desirable.

In one aspect, scopolamine, or an analog thereof, can be administered in an intravenous dosage of from about 2 μg/kg to about 6 μg/kg body weight. Thus, an intravenous dosage of scopolamine, or an analog thereof, can be about 2, 3, 4, 5 or 6 μg/kg body weight, or any dosage within this range. For example, an intravenous dosage of scopolamine, or an analog thereof, can be about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6 μg/kg body weight per day. This dosage can be administered to a subject once daily or in divided dosages throughout a day, as determined by methods known in the art. This dosage can be administered to a subject for one day and then stopped if the subject responds immediately, or the dosage can be administered on a daily basis until a clinical response is noted. It is contemplated that the dosage of scopolamine, or an analog thereof, can be administered as infrequently as once every month or every two months, or at any interval in between, depending on a subject's clinical response to the medication. Thus, if a subject responds to one dosage of scopolamine, or an analog thereof, a person of skill may determine that further dosages of the medication can be withheld. Moreover, if a subject does not respond to the initial dosage and administration of scopolamine, or an analog thereof, a person of skill can administer the medication daily for several days until such response occurs. A person of skill can monitor a subject's clinical response to the administration of scopolamine, or an analog thereof, and administer additional dosages if the subject's mood disorder symptoms reappear after a period of remission. It is contemplated that scopolamine, or an analog thereof, can be administered to a subject with, for example, major mood disorder on a daily basis, on an alternating daily basis, on a weekly basis, on a monthly basis, or at any interval in between.

In another aspect, scopolamine, or an analog thereof, can be administered to a subject transdermally, by using an adherent patch, by using iontophoresis, or by using any other method known to a person of skill. The dosage of scopolamine, or an analog thereof, administered transdermally can be from about 0.5 milligrams to about 1.5 milligrams once every 3 days. Alternatively, the dosage can be given as infrequently as once every 8 weeks. A person of skill, monitoring a subject's clinical response and improvement, can determine the frequency of administration of the medication by methods known in the art.

In another aspect, scopolamine, or an analog thereof, can be administered to a subject intranasally in a dosage of from about 2.5 µg/kg to about 7.5 µg/kg body weight, once daily or in divided doses. The medication can be administered for one day and then stopped if clinical improvement occurs rapidly. Further, the medication can be administered as infrequently as once every 4 to 8 weeks. A person of skill, monitoring a subject's clinical response to the administration of the medication, can adjust the frequency of administration according to methods known in the art.

In another aspect, scopolamine, or an analog thereof, can be administered to a subject intramuscularly in a dosage of from about 3.5 µg/kg to about 10.5 µg/kg body weight, once daily or in divided doses. The medication can be administered for one day and then stopped if clinical improvement occurs rapidly. Furthermore, the medication can be administered as infrequently as once every 4 to 8 weeks. A person of skill, monitoring a subject's clinical response, can adjust the frequency of administration of the medication according to methods known in the art.

In still another aspect, scopolamine, or an analog thereof, can be administered to a subject orally in a dosage of from about 1 milligram to about 10 milligrams, once daily or in divided doses. The medication can be administered for one day and then stopped if clinical improvement occurs rapidly. Furthermore, the medication can be administered as infrequently as once every 4 to 8 weeks. A person of kill, monitoring a subject's clinical response, can adjust the frequency of administration of the medication according to methods known in the art.

The compositions, disclosed in the methods provided, can also optionally include, in addition to scopolamine, or an analog thereof, one or more psychoactive agents. As used herein, a "psychoactive agent" is an agent or drug that affects the mind, emotional state or behavior of a subject. A psychoactive agent can be a mood stabilizing drug. Examples of mood stabilizing drugs include, but are not limited to, lithium, divalproex and other preparations of valproic acid, carbamazepine, and oxcarbazepine. A psychoactive agent can also be an antidepressant drug. Examples of antidepressant drugs include, but are not limited to, fluoxetine, sertraline, luvoxamine, lamotrigine, paroxetine, citalopram, escitalopram, venlafaxine, bupropion, duloxetine, and mirtazapine. Also, a psychoactive agent can be an antipsychotic drug. Examples of antipsychotic drugs include, but are not limited to, olanzepine, risperidone, haloperidol, fluphenazine, aripiprazole, clozapine, quetiapine, ziprasidone, and thiothixene. Furthermore, a psychoactive agent can be an antianxiety drug. Examples of antianxiety drugs include, but are not limited to, buspirone, alprazolam, diazepam, clonazepam, lorazepam, and clorazepate. The dosage and frequency of administration of psychoactive agents are well known to a person of skill in the art.

Provided herein is an inhaler comprising a composition comprising scopolamine, or an analog thereof, in a pharmaceutically acceptable carrier. The inhaler can be a squeeze bottle device, a droplet device, or any other device for aerosolizing the composition for delivering the composition to the upper and/or lower respiratory tracts of a subject in need of treatment. Further provided is a kit comprising an inhaler comprising a composition comprising scopolamine, or an analog thereof, in a pharmaceutically acceptable carrier and instructions regarding using the inhaler. The instructions can have diagrams for teaching a subject how to use the inhaler, in addition to text disclosing the prescribed dosage and frequency of administration of the pharmaceutical composition.

The disclosed methods and compositions can also be used to treat a subject diagnosed with other neuropsychiatric diseases. Examples of neuropsychiatric diseases that can be treated according to the disclosed methods and compositions include, but are not limited to, treatment-resistant major depressive disorder, depressed phase of bipolar disorder, panic disorder, social phobia (social anxiety disorder), post-traumatic stress disorder, and generalized anxiety disorder.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Ten healthy volunteers (HV) (mean age±SE=31.4 years±2.13; 6 females) and eight unmedicated, currently depressed patients meeting the DSM-IV criteria for Major Depressive Disorder (MDD) (n=5; mean age±SE=28 years±3.5; 4 females) or Bipolar Disorder (BD) (n=3; mean age=35 years±5.2; 2 females) participated in this double-blind, randomized dose-finding study, designed to evaluate the acute effects of the antimuscarinic agent, scopolamine, on cognition. Four testing sessions were performed in random order during which participants received a 15-minute intravenous infusion (Ebert, 1998) of a saline placebo and each of three doses of scopolamine, including 2.0, 3.0 and 4.0 µg/kg. Prior to each infusion, a psychiatric interview was performed using the Montgomery & Asberg Depression Rating Scale (MADRS) to monitor depression severity across sessions. Participants were monitored continuously for the development of clinically relevant side effects. Sessions were scheduled a minimum of 3 days apart and a maximum of 5 days apart when possible. Follow-up psychiatric interviews were obtained when patients were available.

Results

MADRS scores were compared across sessions in series irrespective of session dose (Table 1), as inherently over time individuals are receiving doses of scopolamine. No change in MADRS was observed in the healthy volunteer (HV) group.

Repeated measures ANOVA showed a significant difference in MADRS scores across sessions (F=3.41, p=0.036) in the patient group. Post-hoc t-test comparisons demonstrate that the MADRS scores were significantly lower following session three (p=0.03) and session four (p=0.01) as compared to session one baseline measures. Differences between MADRS scores obtained in sessions two and four trended towards significance (p=0.054).

The antidepressant effect of each scopolamine dose was evaluated in the patient group by using t-tests to compare MADRS scores obtained at baseline (as evaluated in session one prior to infusion) to each MADRS score obtained in the session following the administration of each specific dose. For example, the effect of the 2.0 µg/kg was determined by comparing the baseline MADRS score to that obtained in the session following the administration of 2.0 µg/kg of scopolamine (Table II). Comparisons also were made between MADRS scores obtained before and after each specific dose. For example, the score obtained immediately prior to the administration of 2.0 µg/kg of scopolamine (i.e., pre-) was compared to the score obtained in the next session, 3 to 5 days later, prior to further treatment (i.e., post-). Post evaluations for the last session were provided by the follow-up psychiatric interviews when available. MADRS scores obtained post 4.0 µg/kg of scopolamine were significantly lower than both baseline (p=0.0015) and pre-4.0 µg/kg measures (p=0.018). No other differences were significant.

In summary, the MADRS scores decreased dramatically across sessions in the patient group, demonstrating robust and rapid antidepressant effects. Evaluation by dose demonstrated that the antidepressant effects occurred primarily following the 4.0 µg/kg dose of scopolamine. However, as this experimental design was not ideal to characterize an antidepressant effect, a second study was designed to more appropriately assess the antidepressant efficacy of scopolamine.

Example 2

Eighteen (11 females) healthy volunteers (HV) (mean age±SE=33±1.8) and 15 unmedicated, currently depressed patients meeting the DSM-IV criteria for Major Depressive Disorder (MDD) (n=6; 4F; Mean age±SE=39.8±2.04) or Bipolar Disorder (BD) (n=9; 7F; Mean age±SE=29.8±3.3) participated in this double-blind, placebo-controlled, randomized cross-over study, designed to evaluate the effects of the antimuscarinic agent, scopolamine, on symptoms of depression. Patient diagnosis and features that contribute to prognosis, including history of response to conventional treatment, chronicity and comorbid anxiety disorders, are summarized in Table III. Of our 15 patients, 11 had a poor prognosis.

During each of seven sessions, subjects received a 15 minute intravenous infusion of either a placebo saline solution, or 4.0 µg/kg of scopolamine. Session one was designed to be single-blind during which all subjects received a placebo infusion to allow for a baseline evaluation in all subjects. Subsequently, individuals were randomized into either an P/S or S/P double-blind design whereby P is defined as a series of three sessions during which participants received placebo and S is defined as a series of three sessions during which participants received scopolamine. All subjects received four placebo infusions and three scopolamine infusions (see FIG. 1). Prior to each infusion, unstructured psychiatric interviews were completed using the MADRS and the Hamilton Anxiety Scale. Sessions were scheduled a minimum of 3 days apart and a maximum of 5 days apart when possible. Follow-up psychiatric interviews were obtained to assess the effects of session seven. Findings from 4 evaluations were used to evaluate the effect of scopolamine on symptoms of depression and anxiety, including session 1 (baseline 1), session 2 (baseline 2), session 5 (last evaluation in Block 1), and follow-up (last evaluation in Block 2). Repeated measures ANOVA was used to evaluate session differences, group differences and session X group effects. In the presence of significant ANOVA results, t-tests were used for within and between group comparisons to identify specific effects.

Results

Mean MADRS scores (±SE) are shown in FIG. 2 for the two patient groups. The patients randomized into the P/S series (placebo/scopolamine) are shown in hatched bars and the patients in the S/P series (scopolamine/placebo) are shown in white bars. Repeated measures ANOVA showed a significant group by evaluation interaction (F=10.36, p<0.0001). Individual t-test comparisons indicated that the two groups did not differ at baseline 1 or baseline 2 (p>0.60). The groups did differ significantly at the last evaluation of Block 1 (t=5.3; p<0.0001) with the S/P group scoring significantly lower on depression severity than the P/S group. Within group analyses demonstrate that, compared to baseline measures, the P/S group had significantly lower depression severity scores only at the end of Block 2 (during which they received scopolamine) as compared to baseline measures (t=4.2, p<0.005; t=4.1, p<0.005, respectively), and compared to the end of Block 1 (t=4.1, p<0.005), with no change observed during block 1 (duringwhich they received placebo) relative to baseline (p>0.6). The S/P group had significantly lower depression severity scores at the end of Block 1 (during which they received scopolamine) as compared to baseline 1 (t=4.45, p<0.005) and to baseline 2 (t=4.7, p<0.005), and at the end of Block 2 as compared to baseline measures (t=4.5, p<0.005; t=4.9, p<0.005, respectively).

Mean Ham-Anxiety scores (±SE) are shown in FIG. 3 for the two patient groups. Again, the patients randomized into the P/S series (placebo/scopolamine) are shown in hatched bars and the patients in the S/P series (scopolamine/placebo) are shown in white bars. Repeated measures ANOVA showed a significant group by evaluation interaction (F=4.29, p=0.01). Using t-test comparison, the groups were found to differ significantly at the last evaluation of Block 1 (t=7.29, p=0.04) with the S/P group scoring significantly lower on symptoms of anxiety than the P/S group. Within group analyses demonstrate that, compared to baseline measures, the P/S group had significantly lower anxiety ratings at the end of Block 2 (during which they received scopolamine) as compared to baseline 1 (t=6.4, p<0.001) and to baseline 2 (t=3.3, p=0.02), and compared to the end of Block 1 (during which they received placebo) (t=5.4, p=0.002), with no change observed during Block 1 relative to baseline (p>0.5). The S/P group had significantly lower anxiety ratings at the end of Block 1 as compared to baseline measures (t=3.9, p<0.01; t=4.5, p<0.01, respectively), and at the end of Block 2 as compared to baseline (t=3.4, p=0.01; t=3.5, p=0.01, respectively).

These results demonstrate that scopolamine is producing rapid and robust effects on symptoms of depression and anxiety. Importantly, study 2 replicates the major finding observed in study 1, that scopolamine improves symptoms of depression. Moreover, the design employed in study 2 also allows for a within study replication by utilizing two groups that receive scopolamine under different schedules. The P/S group showed no change in symptoms of depression or anxiety during Block 1 while receiving placebo, but did show dramatic improvement in depression and anxiety scores during Block 2, during which they were receiving scopolamine. Importantly, this finding demonstrates that symptoms of depression and anxiety did not change in association with placebo conditions. The results from group S/P show both rapid effects to scopolamine (as demonstrated in Block 1), but they also demonstrate that the antidepressant effects persist as the group continues to obtain lower depression and anxiety scores in Block 2, during which they receive placebo. Finally, the patients showed these dramatic improvements in symptoms despite the fact that the majority of the patients had a poor prognosis, suggesting that scopolamine can be beneficial even for those patients who are resistant to treatment.

Throughout this application, various publications are referenced. The disclosures of hese publications in their entireties are hereby incorporated by reference into this application in order to more fully describe the state of the art to which this invention pertains.

REFERNCES

1. Janowsky, E. C., C. Risch, and D. S. Janowsky, *Effects of anesthesia on patients taking psychotropic drugs*. Journal of Clinical Psychopharmacology, 1981. 1(1): p. 14-20.
2. Janowsky, D. S., M. K. el-Yousef, and J. M. Davis, *Acetylcholine and depression*. Psychosomatic Medicine, 1974. 36(3): p. 248-57.
3. Janowsky, D. S., et al., *Cholinergic reversal of manic symptoms*. Lancet, 1972. 1(7762): p. 1236-7.
4. Davis, K. L., et al., *Physostigmine in mania*. Archives of General Psychiatry, 1978. 35(1): p. 119-22.
5. Risch, S. C., N. H. Kalin, and D. S. Janowsky, *Cholinergic challenges in affective illness: behavioral and neuroendocrine correlates*. Journal of Clinical Psychopharmacology, 1981. 1(4): p.186-92.
6. Nurnberger, J. I., Jr., et al., *Behavioral, physiological, and neuroendocrine responses to arecoline in normal twins and "well state" bipolar patients*. Psychiatry Research, 1983. 9(3): p. 191-200.
7. Raisman, R., M. Briley, and S. Z. Langer, *Specific tricyclic antidepressant binding sites in rat brain*. Nature, 1979. 281(5727): p. 148-50.
8. Richelson, E., *Antimuscarinic and other receptor-blocking properties of antidepressants*. Mayo Clinic Proceedings, 1983. 58(1): p. 40-6.
9. Stanton, T., et al., *Antagonism of the five cloned human muscarinic cholinergic receptors expressed in CHO-K1 cells by antidepressants and antihistaminics*. Biochemical Pharmacology, 1993. 45(11): p. 2352-4.
10. Dilsaver, S. C., *Pathophysiology of "cholinoceptor supersensitivity" in affective disorders*. Biological Psychiatry, 1986. 21(8-9): p. 813-29.
11. Janowsky, D. S., et al., *Effects of physostigmine on pulse, blood pressure, and serum epinephrine levels*. American Journal of Psychiatry, 1985. 142(6): p. 738-40.
12. Janowsky, D. S. and D. H. Overstreet, *The role of acetylcholine mechanisms in mood disorders*. Psychopharmacology: The Fourth Generation of progress, ed. D. J. Kupfer. 1995, New York: Raven Press.
13. Rubin, R. T., et al., *Hypothalamo-pituitary-adrenal cortical responses to low-dose physostigmine and arginine vasopressin administration: sex differences between major depressives and matched control subjects*. Psychiatry Research, 1999. 89(1): p. 1-20.
14. Schatzberg, A. F., *Pharmacologic treatment of major depression: are two mechanisms really better than one?* J Clin Psychiatry, 2004. 65: p. 3-4.
15. Delgado, P. L., *How antidepressants help depression: mechanisms of action and clinical response*. J Clin Psychiatry, 2004. 65: p. 25-30.
16. Pacher, P. and V. Kecskemeti, *Trends in the development of new antidepressants. Is there a light at the end of the tunnel?* Current Medicinal Chemistry, 2004. 11: p. 925-943.
17. Preskom, S. H., *Rational drug discovery and SSRI's*. In: Clinical Pharmacology of SSRI's. Ed: S. H. Preskorn, Professional Communications, Inc., 1996.

TABLE I

| Patients | Session 1 | Session 2 | Session 3 | Session 4 | Follow-up |
|---|---|---|---|---|---|
| HV (mean) | 0± | 0± | 0± | 0± | NA |
| MDD1 | $23^b$ | $32^c$ | $25^a$ | $28^d$ | 9 |
| MDD2 | $29^c$ | $18^b$ | $14^a$ | $11^d$ | 14 |
| MDD3 | $29^b$ | $29^c$ | $22^d$ | $17^a$ | |
| MDD4 | $32^c$ | $15^d$ | $7^a$ | $7^b$ | |
| MDD5 | $37^c$ | $36^d$ | $35^b$ | $35^a$ | |
| BD1 | $37^c$ | $44^a$ | $34^d$ | $22^b$ | 37 |
| BD2 | $21^c$ | $25^a$ | $31^b$ | $32^d$ | 16 |
| BD3 | $24^a$ | $14^b$ | $4^c$ | $8^d$ | 2 |
| Pt. MEAN | 29 | 26.6 | 21.5 | 20.0* | 15.6* |

MDD—Major Depressive Disorder
BD—Bipolar Disorder
$^a$placebo session
$^b$2 µg/kg
$^c$3 µg/kg
$^d$4 µg/kg
*significantly less than baseline, p < 0.05

TABLE II

| Patients | Baseline | Pre 0 µg/kg | Post 0 µg/kg | Pre 2 µg/kg | Post 2 µg/kg | Pre 3 µg/kg | Post 3 µg/kg | Pre 4 g/kg | Post 4 µg/kg |
|---|---|---|---|---|---|---|---|---|---|
| MDD1 | 23 | 25 | 28 | 23 | 32 | 32 | 25 | 28 | 9 |
| MDD2 | 29 | 14 | 11 | 18 | 14 | 29 | 18 | 11 | 14 |
| MDD3 | 29 | 17 | / | 29 | 29 | 29 | 22 | 22 | 17 |
| MDD4 | 32 | 7 | 7 | 7 | / | 32 | 15 | 15 | 7 |
| MDD5 | 37 | 35 | / | 35 | 35 | 37 | 36 | 36 | 35 |
| BD1 | 37 | 44 | 34 | 22 | 37 | 37 | 44 | 34 | 22 |
| BD2 | 21 | 25 | 31 | 31 | 32 | 21 | 25 | 32 | 16 |
| BD3 | 24 | 24 | 14 | 14 | 4 | 4 | 8 | 8 | 2 |
| MEAN | 29.00 | 23.88 | 20.83 | 22.38 | 26.14 | 27.63 | 24.13 | 23.25 | 15.25[#]* |

MDD—Major Depressive Disorder
BD—Bipolar Disorder
*significantly less than baseline, p = 0.0015
[#]post session significantly less than pre-session (i.e. within dose), p = 0.018
/ missing value- pre measure obtained during session 4

TABLE III

Prognosis for Patient Groups

| Patient | Response to Treatment | Chronicity (>2 years) | Comorbid Anxiety | Prognosis | Diagnosis |
|---|---|---|---|---|---|
| 1 | Never treated | 23 years | Simple phobia | Poor | MDD |
| 2 | Not responsive | 4 years | SAD | Poor | BDII |
| 3 | Not responsive | Since childhood | OCD | Poor | BDII |
| 4 | Never treated | No | PTSD | Poor | BDII |
| 5 | Not responsive | 27 years | SAD/panic disorder | Poor | MDD |
| 6 | Response OK | No | No | Good | BDI |
| 7 | Response OK | No | No | Good | MDD |
| 8 | Never treated | 11 years | GAD | Poor | MDD |
| 9 | Response OK | 5 years | No | Poor | BDI |
| 10 | Not responsive | Since childhood | No | Poor | BDI |
| 11 | Responsive | No | No | Good | BDII |
| 12 | Responsive | 16 years | GAD | Poor | MDD |
| 13 | Never treated | No | No | Good | MDD |
| 14 | Not responsive | 4 years | No | Poor | BDII |
| 15 | Never treated | 4 years | SAD | Poor | MDD |

SAD—Social Anxiety Disorder
OCD—Obsessive Compulsive Disorder
PTSD—Post Traumatic Stress Disorder
GAD—Generalized Anxiety Disorder
MDD—Major Depressive Disorder
BD—Bipolar Disorder It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating major depressive disorder in a subject diagnosed with major depressive disorder, consisting of administering to the subject a composition consisting of a therapeutically effective amount of scopolamine, a pharmaceutically acceptable salt or ester thereof, in a pharmaceutically acceptable carrier, whereby the administration of the composition treats major depressive disorder in the subject.

2. The method of claim 1, wherein the subject is a mammal.

3. The method of claim 2, wherein the mammal is a human.

4. The method of claim 1, wherein the scopolamine or a pharmaceutically acceptable salt or ester thereof is administered in a dosage of from 2 µg/kg to 6 µg/kg of body weight.

5. The method of claim 1, wherein the composition is administered intravenously.

6. The method of claim 1, wherein the composition is administered transdermally.

7. The method of claim 1, wherein the composition is administered intranasally.

8. The method of claim 1, wherein the composition is administered orally.

9. A method of treating major depressive disorder in a subject diagnosed with major depressive disorder, comprising administering to the subject a composition consisting of a therapeutically effective amount of scopolamine, a scopolamine analog or a pharmaceutically acceptable salt or ester thereof, in a pharmaceutically acceptable carrier, whereby the administration of the composition treats major depressive disorder in the subject in which clinical improvement is observed within 3-5 days.

10. The method of claim 9, wherein the scopolamine analog is selected from the group consisting of scopolamine methylbromide, tiotropium, scopolamine butylbromide, atropine, ipratropium, scopolamine hydrobromide and pharmaceutically acceptable salts or esters thereof.

11. The method of claim 9, wherein the subject is a mammal.

12. The method of claim 11, wherein the mammal is a human.

13. The method of claim 9, wherein scopolamine or pharmaceutically acceptable salt or ester thereof is administered in a dosage of from 2 µg/kg to 6 µg/kg of body weight.

14. The method of claim 9, wherein the composition is administered intravenously.

15. The method of claim 9, wherein the composition is administered transdermally.

16. The method of claim 9, wherein the composition is administered intranasally.

17. The method of claim 9, wherein the composition is administered orally.

18. A method of treating major depressive disorder in a subject diagnosed with major depressive disorder, consisting of administering to the subject an intravenous dosage of a composition consisting of from 2 µg/kg to 6 µg/kg of body weight scopolamine or a pharmaceutically acceptable salt or ester thereof for one day.

* * * * *